United States Patent
Mimura et al.

(10) Patent No.: US 9,603,788 B2
(45) Date of Patent: Mar. 28, 2017

(54) HAIR STYLING COMPOSITION

(71) Applicant: MILBON CO., LTD., Osaka-shi, Osaka (JP)

(72) Inventors: Marina Mimura, Osaka (JP); Yusuke Takino, Osaka (JP); Yohei Matsumoto, Osaka (JP)

(73) Assignee: MILBON CO., LTD., Osaka (JP)

( * ) Notice: Subject to any disclaimer, the term of this patent is extended or adjusted under 35 U.S.C. 154(b) by 0 days.

(21) Appl. No.: 14/546,346

(22) Filed: Nov. 18, 2014

(65) Prior Publication Data

US 2015/0147285 A1    May 28, 2015

(30) Foreign Application Priority Data

Nov. 26, 2013  (JP) .................................. 2013-243436

(51) Int. Cl.
| | | |
|---|---|---|
| A61K 8/92 | (2006.01) | |
| A61K 8/86 | (2006.01) | |
| A61Q 5/06 | (2006.01) | |
| A61K 8/81 | (2006.01) | |
| A61K 8/73 | (2006.01) | |

(52) U.S. Cl.
CPC .............. *A61K 8/922* (2013.01); *A61K 8/731* (2013.01); *A61K 8/8135* (2013.01); *A61K 8/8158* (2013.01); *A61K 8/86* (2013.01); *A61K 8/927* (2013.01); *A61Q 5/06* (2013.01); *A61K 2800/48* (2013.01)

(58) Field of Classification Search
None
See application file for complete search history.

(56) References Cited

U.S. PATENT DOCUMENTS

| | | | | |
|---|---|---|---|---|
| 3,577,518 A | * | 5/1971 | Shepherd | A61K 8/8152 424/47 |
| 5,194,260 A | * | 3/1993 | Grollier | A61K 8/044 424/401 |
| 5,306,488 A | * | 4/1994 | Vanlerberghe | A61K 8/044 424/70.31 |
| 6,066,316 A | * | 5/2000 | Shiojima | A61K 8/044 424/401 |
| 2002/0061320 A1 | * | 5/2002 | Belli | A61K 8/73 424/401 |
| 2003/0059377 A1 | * | 3/2003 | Riley | 424/47 |
| 2005/0095212 A1 | * | 5/2005 | Hirano | A61K 8/42 424/70.11 |
| 2014/0105845 A1 | * | 4/2014 | Bui et al. | 424/70.7 |

FOREIGN PATENT DOCUMENTS

| | | |
|---|---|---|
| JP | 2011-93846 | 5/2011 |
| JP | 2011-98936 | 5/2011 |
| JP | 2012087096 A * | 5/2012 |

OTHER PUBLICATIONS

English machine translation of JP 2012087096 A (published May 2012), Patent Translate powered by EPO and Google, p. 1-9.*
Sigma-Aldrich, "Polyoxyethylene 20 Cetyl Ether," Product Information, Feb. 6, 2003, p. 1.*

* cited by examiner

*Primary Examiner* — Tracy Vivlemore
*Assistant Examiner* — Monica Shin
(74) *Attorney, Agent, or Firm* — Wenderoth, Lind & Ponack, L.L.P.

(57) ABSTRACT

An object of the present invention is to provide a hair styling composition formulated to make hair styling easy and to add wet-look shine to hair. The hair styling composition which achieves the above object contains (A) a thickener, (B) a hair fixative polymer and/or a liquid oil, (C) a wax particle dispersion, and (D) water. In the hair styling composition of the present invention, the wax particle dispersion (C) is preferably an Euphorbia Cerifera (Candelilla) wax particle dispersion or a beeswax particle dispersion, or preferably contains wax, at least one nonionic surfactant selected from the group consisting of polyoxyethylene cetyl ether and polyoxyethylene polyoxypropylene cetyl ether, and water.

10 Claims, No Drawings

HAIR STYLING COMPOSITION

CROSS-REFERENCES TO RELATED APPLICATIONS

This application claims priority to and the benefit of Japanese Patent Application No. 2013-243436 filed Nov. 26, 2013, the entire contents of which is incorporated herein by reference.

BACKGROUND OF THE INVENTION (1) Field of the Invention

The present invention relates to a hair styling composition formulated to make hair styling easy and to add wet-look shine to hair.

(2) Description of the Related Art

There have been developed a variety of hair styling compositions with different ingredients. For example, known products contain an ingredient for increasing hair-setting power, such as wax or hydrocarbons, or a polymer (water-soluble polymer) capable of functioning as a thickener (see, for example, JP 2011-93846 A and JP 2011-98936 A).

Hair styling compositions containing a thickener such as a water-soluble polymer can add, for example, good shine to hair. However, for example, when a hair fixative polymer or a liquid oil is added into the hair styling compositions in addition to a thickener in order to further increase hair-setting power, compositions containing a hair fixative polymer may cause hair to fix together quickly, and compositions containing a liquid oil may cause hair to appear oily and heavy. Therefore, in these cases, it may be difficult to style hair as desired.

Under these circumstances, there has been a demand for a technique for developing a hair styling composition having the ability to make hair styling easy without impairing the function to add good shine to hair.

SUMMARY OF THE INVENTION

The present invention has been made in view of the above background, and an object of the present invention is to provide a hair styling composition formulated to make hair styling easy and to add wet-look shine to hair.

The hair styling composition of the present invention, which achieves the above object, contains (A) a thickener, (B) a hair fixative polymer and/or a liquid oil, (C) a wax particle dispersion, and (D) water.

The present invention makes it possible to provide a hair styling composition formulated to make hair styling easy and to add wet-look shine to hair.

DETAILED DESCRIPTION OF THE INVENTION

As mentioned above, when a hair fixative polymer or a liquid oil is added to a hair styling composition containing a thickener, its ability to make hair styling easy can be impaired.

According to the present invention, the hair styling composition containing (A) a thickener, (B) a hair fixative polymer and/or a liquid oil, and (D) water is supplemented with (C) an additional ingredient that is a dispersion containing finely dispersed wax in a dispersion medium, which makes it possible to ensure the function to add wet-look shine to hair and also to improve the ability to make hair styling easy.

The thickener as the ingredient (A) can not only serve to adjust the viscosity of the hair styling composition to a level at which the hair styling composition can be well handled, but also work together with the ingredients (B), (C), and (D) to add wet-look shine to hair after hair styling.

Examples of the thickener include hydroxypropyl starch phosphate, ethyl hydroxyethyl cellulose, methyl hydroxyethyl cellulose, stearoxy hydroxypropyl methyl cellulose, carrageenan, xanthan gum, carboxymethyl cellulose sodium, cationized cellulose, sodium alginate, polyvinyl alcohol, a salt of a carboxyvinyl polymer, sodium polyacrylate, polyacrylamide, a salt of an acrylic acid/alkyl methacrylate copolymer (in which the alkyl group of alkyl methacrylate has 10 to 30 carbon atoms), hydroxyethyl cellulose, hydroxypropyl cellulose, Tamarindus Indica seed gum, and highly polymerized polyethylene glycol (300,000 or more in average molecular weight such as 2,000,000 in average molecular weight). These thickeners may be used singly or in combination of two or more. Of these thickeners, a salt of a carboxyvinyl polymer, a salt of an acrylic acid/alkyl methacrylate copolymer, hydroxyethyl cellulose, highly polymerized polyethylene glycol (2,000,000 in average molecular weight), hydroxypropyl cellulose, and Tamarindus Indica seed gum are preferred, and a salt of a carboxyvinyl polymer is particularly preferred because of its particularly high thickening effect.

The thickeners in salt form (i.e., carboxymethyl cellulose sodium, sodium alginate, a salt of a carboxyvinyl polymer, sodium polyacrylate, a salt of an acrylic acid/alkyl methacrylate copolymer etc.) may be added into a hair styling composition after the salt formation, or the thickeners in salt form may be formed in a hair styling composition by mixing an acidic polymer (i.e, carboxymethyl cellulose, alginic acid, a carboxyvinyl polymer, polyacrylic acid, an acrylic acid/alkyl methacrylate copolymer etc.) with an alkaline agent for the neutralization.

Examples of alkaline agents for the neutralization of the acidic polymer include organic alkalis such as 2-amino-2-methyl-1-propanol, monoethanolamine, triethanolamine, monoisopropanolamine, diisopropanolamine, and arginine; and inorganic alkalis such as alkali metal hydroxides (such as potassium hydroxide and sodium hydroxide), ammonia, sodium hydrogen carbonate, and sodium carbonate. These may be used singly or in combination of two or more.

The content of the thickener as the ingredient (A) in the hair styling composition is preferably 0.05% by mass or more, more preferably 0.1% by mass or more in order to provide the above function more successfully. However, if the content of the ingredient (A) in the hair styling composition is too high, the composition may tend to give a stiff feel to hair. Therefore, the content of the thickener as the ingredient (A) in the hair styling composition is preferably 3% by mass or less, more preferably 2% by mass or less.

When a thickener in salt form is formed in a hair styling composition, the above acidic polymer and alkaline agent may be added into a hair styling composition in such amounts that the content of the thickener in salt form is in the range of the above content, and the alkaline agent may be added in a sufficient amount to neutralize the above acidic polymer.

The hair styling composition of the present invention contains at least one of a hair fixative polymer and a liquid oil as the ingredient (B). The function of the ingredient (B) is mainly to increase the hair-setting power of the hair styling composition.

The hair styling composition of the present invention may contain only one of the hair fixative polymer and the liquid oil or both the hair fixative polymer and the liquid oil.

An anionic, amphoteric, or nonionic polymer or copolymer, or a urethane resin may be used as the hair fixative polymer. The anionic hair fixative polymers have a monomer such as an acrylic group-containing polymerizable vinyl monomer (such as acrylic acid or acrylic ester), a methacrylic group-containing polymerizable vinyl monomer (such as methacrylic acid or methacrylic ester), or any other polymerizable vinyl monomer (such as vinylpyrrolidone, vinyl acetate, or vinyl methyl ether).

Examples of the hair fixative polymer include polyvinylpyrrolidone, polyvinyl acetate, hydroxyethyl acrylate/butyl acrylate/methoxymethyl acrylate copolymers, hydroxyethyl acrylate/methoxyethyl acrylate copolymers, acrylic acid/acrylic acid amide/ethyl acrylate copolymers, alkyl acrylate copolymers, acrylic acid octyl amide/hydroxypropyl acrylate/butylaminoethyl methacrylate copolymers, butyl acrylate/hydroxyethyl methacrylate copolymers, acrylic resin alkanolamines (such as (alkyl acrylate/diacetone acrylamide) copolymer AMP, alkyl acrylate copolymer AMP, (alkyl acrylate/diacetone acrylamide) copolymer AMPD, and (acrylate/alkyl (C1-C18) acrylate/alkyl (C1-C8) acrylamide) copolymer AMP), acrylic alkyl ester/methacrylic alkyl ester/diacetone acrylamide/methacrylic acid copolymers, hydroxyethyl acrylate/butyl acrylate/methoxyethyl acrylate copolymers, alkyl acrylate/vinyl acetate copolymers, vinyl acetate/vinylpyrrolidone copolymers, vinyl methyl ether/ethyl maleate copolymers, vinyl methyl ether/butyl maleate copolymers, vinyl acetate/crotonic acid copolymers, N-methacryloyloxyethyl-N,N-dimethylammonium-N-methylcarboxybetaine/alkyl methacrylate copolymers, vinylpyrrolidone/N,N-dimethylaminoethyl methacrylate copolymer diethyl sulfate salt, acrylate polymers, acrylate copolymer AMP, and polyurethane-14. These may be used singly or in combination of two or more. Of these hair fixative polymers, a polymer or copolymer of an acrylic group-containing polymerizable vinyl monomer is preferred, (alkyl acrylate/diacetone acrylamide) copolymer AMP and hydroxyethyl acrylate/methoxyethyl acrylate copolymer are more preferred, and (alkyl acrylate/diacetone acrylamide) copolymer AMP is particularly preferred because it can be more effective in increasing the hair-setting power.

When the hair fixative polymer is used as the ingredient (B), the content of the hair fixative polymer in the hair styling composition is preferably 0.05% by mass or more, more preferably 0.1% by mass or more in order to successfully ensure the effect of its use. Meanwhile, if the amount of the hair fixative polymer in the hair styling composition is too large, the hair fixative polymer may easily solidify and tend to degrade the handleability during the application of the hair styling composition. Therefore, when the hair fixative polymer is used as the ingredient (B), the content thereof in the hair styling composition is preferably 10% by mass or less, more preferably 5% by mass or less.

Examples of the liquid oil include vegetable oils, hydrocarbons, ethers, silicones, and ester oils.

Examples of vegetable oils include *simmondsia chinensis* (jojoba) seed oil, *butyrospermum parkii* (shea butter) oil, rose hip oil, *helianthus annuus* (sunflower) seed oil, cottonseed (*gossypium*) oil, *argania spinosa* kernel oil, *camellia japonica* seed oil, *camellia kissi* seed oil, *persea gratissima* (avocado) oil, *prunus amygdalus dulcis* (sweet almond) oil, *olea europaea* (olive) fruit oil, *sesamum indicum* (sesame) seed oil, *oryza sativa* (rice) bran oil, *carthamus tinctorius* (safflower) seed oil, *glycine soja* (soybean) oil, *macadamia ternifolia* seed oil, *zea mays* (corn) oil, *brassica campestris* (rapeseed) oil, *prunus armeniaca* (apricot) kernel oil, *elaeis guineensis* (palm) oil, *ricinus communis* (castor) seed oil, *vitis vinifera* (grape) seed oil, *cocos nucifera* (coconut) oil, hydrogenated oil, and other vegetable oils. Examples of hydrocarbons include light isoparaffin, light liquid isoparaffin, squalane, liquid paraffin, and liquid isoparaffin.

Examples of ethers include isostearyl glyceryl ether, ethylene glycol monoethyl ether, glycerin monocetyl ether, and monooleyl glyceryl ether. Examples of silicones include dimethyl silicone (such as dimethicone), dimethiconol, cyclic silicones, polyether-modified silicones, amino-modified silicones, polyglycerin-modified silicones, and methyl phenyl silicone.

Examples of ester oils include isopropyl myristate, butyl myristate, isopropyl palmitate, cetyl caprylate, oleyl oleate, isostearyl laurate, isotridecyl myristate, 2-hexyldecyl myristate, isostearyl myristate, 2-octyldodecyl myristate, 2-ethylhexyl palmitate, 2-hexyldecyl palmitate, isostearyl palmitate, 2-diethylhexyl stearate, 2-hexyldecyl stearate, ethyl isostearate, isopropyl isostearate, cetyl 2-ethylhexanoate, hexyl isostearate, ethylene glycol di-2-ethylhexanoate, propylene glycol dicaprylate, propylene glycol di(capryl caprylate), glyceryl tricaprylate, glyceryl tri-2-ethylhexanoate, glyceryl tri(capryl caprylate), pentaerythritol tetra-2-ethylhexanoate, pentaerythritol tetraisostearate, 2-octyldodecyl neopentanoate, 2-hexyldecyl 2-ethylhexanoate, isostearyl 2-ethylhexanoate, 2-ethylhexyl isononanoate, 2-hexyldecyl dimethyloctanoate, 2-octyldodecyl dimethyloctanoate, 2-ethylhexyl isopalmitate, 2-hexyldecyl isostearate, isostearyl isostearate, 2-octyldodecyl isostearate, lauryl lactate, 2-octyldodecyl lactate, dicaprylyl carbonate, tri-2-ethylhexyl citrate, distearyl malate, di-2-ethylhexyl succinate, diisopropyl adipate, diisobutyl adipate, di-2-ethylhexyl adipate, diethyl sebacate, diisopropyl sebacate, di-2-ethylhexyl sebacate, dibutyloctyl sebacate, isocetyl 12-stearoylhydroxystearate, stearyl 12-stearoylhydroxystearate, and isostearyl 12-stearoylhydroxystearate.

As the liquid oil used in the hair styling composition of the present invention, liquid paraffin, *butyrospermum parkii* (shea butter) oil, dimethicone, and cetyl 2-ethylhexanoate are preferred, and liquid paraffin is particularly preferred.

When the liquid oil is used as the ingredient (B), the content of the liquid oil in the hair styling composition is preferably 0.01% by mass or more, more preferably 0.1% by mass or more in order to successfully ensure the effect of its use. Meanwhile, if the amount of the liquid oil in the hair styling composition is too large, the hair styling composition may be difficult to prepare. Therefore, when the liquid oil is used as the ingredient (B), the content thereof in the hair styling composition is preferably 60% by mass or less, more preferably 50% by mass or less.

When the hair styling composition of the present invention contains both a hair fixative polymer and a liquid oil as the ingredient (B), each content of the hair fixative polymer and the liquid oil may be the content as described above, and the content of the ingredient (B) in the hair styling composition may be the total amount of the hair fixative polymer and the liquid oil.

In the hair styling composition of the present invention, the wax particle dispersion as the ingredient (C) is a dispersion containing finely dispersed wax in a dispersion medium.

Examples of wax for the wax particle dispersion include Euphorbia Cerifera (Candelilla) wax and beeswax. Water is used as a dispersion medium for the wax particle dispersion.

The wax particle dispersion preferably further contains at least one nonionic surfactant selected from the group consisting of polyoxyethylene cetyl ether (a polyethylene glycol ether of cetyl alcohol) and polyoxyethylene polyoxypropylene cetyl ether (a polyoxypropylene, polyoxyethylene ether of cetyl alcohol). The nonionic surfactant can function to stabilize the state of the dispersed wax in the dispersion.

The nonionic surfactant that may be added to the wax particle dispersion preferably has a hydrophile-lipophile balance (HLB) value of 11.0 to 16.0. Alternatively, two or more nonionic surfactants each with an HLB value out of this range may also be used so as to provide a weighted average HLB value of 11.0 to 16.0.

As used herein, the HLB value of the nonionic surfactant is the value determined by the procedures (1) and (2) below.
(1) Different emulsions with the composition shown below are prepared by the preparation method described below using "a" parts by mass of the nonionic surfactant and "b" parts by mass of sorbitan monostearate (NIKKOL SS-10MV manufactured by Nikko Chemicals Co., Ltd., 4.7 in HLB value) as an emulsifier in different a/b ratios.
(2) After the different emulsions are temporarily allowed to stand, the particle size of oil droplets in each emulsion is determined, and the a/b ratio when the particle size is minimum is determined. The HLB value is calculated from the formula (10.5−4.7×b/4)×(4/a) using a and b when the a/b ratio is such that the particle size is minimum.

Emulsion Composition:

| | |
|---|---|
| Liquid paraffin (as an oil phase) | 40% by mass |
| Emulsifier | a + b = 4% by mass |
| Water | 56% by mass |

Method for Preparing Emulsion:

The aqueous phase at 80° C. or higher is added to the liquid paraffin with being stirred and heated at about 80° C., and then emulsified. Subsequently, the emulsion is continued to be stirred under cooling and then allowed to stand at 40° C.

Examples of the polyoxyethylene cetyl ether (a polyethylene glycol ether of cetyl alcohol) include POE (5.5) cetyl ether, POE (7) cetyl ether, POE (10) cetyl ether, POE (15) cetyl ether, and POE (20) cetyl ether, wherein the number between "POE" and "cetyl ether" means the average number of moles of added ethylene oxide.

These polyoxyethylene cetyl ethers may be commercially available products such as NIKKOL BC-5.5, NIKKOL BC-7, NIKKOL BC-10, NIKKOL BC-15, and NIKKOL BC-20 manufactured by Nikko Chemicals Co., Ltd.

Examples of the polyoxyethylene polyoxypropylene cetyl ether (a polyoxypropylene, polyoxyethylene ether of cetyl alcohol) include POE (1) POP (4) cetyl ether, POE (10) POP (4) cetyl ether, POE (20) POP (4) cetyl ether, POE (1) POP (8) cetyl ether, and POE (20) POP (8) cetyl ether, wherein the numbers after "POE" and "POP" respectively, for each polyoxyethylene polyoxypropylene cetyl ether mean the average number of moles of added ethylene oxide and the average number of moles of added propylene oxide, respectively.

These polyoxyethylene polyoxypropylene cetyl ethers may be commercially available products such as NIKKOL PBC-31, NIKKOL PBC-33, NIKKOL PBC-34, NIKKOL PBC-41, and NIKKOL PBC-44 manufactured by Nikko Chemicals Co., Ltd.

In the wax particle dispersion, the dispersed wax particles preferably have a volume average particle size of 500 nm or less, more preferably 300 nm or less, even more preferably 100 nm or less, further more preferably 50 nm or less, so that the ability of the hair styling composition to make hair styling easy can be more successfully increased. As used herein, the volume average particle size of wax in the wax particle dispersion is the value determined using a laser diffraction method or dynamic light scattering.

The content of wax in the wax particle dispersion is preferably 3% by mass or more, more preferably 5% by mass or more, even more preferably 10% by mass or more, and preferably 30% by mass or less, more preferably 25% by mass or less, even more preferably 20% by mass or less.

Based on 100 parts by mass of the wax, the content of the nonionic surfactant in the wax particle dispersion is preferably 20 parts by mass or more, more preferably 40 parts by mass or more, even more preferably 80 parts by mass or more, and preferably 300 parts by mass or less, more preferably 250 parts by mass or less, even more preferably 120 parts by mass or less. When the nonionic surfactant is added in such an amount, the size of the dispersed wax particles in the dispersion can be reduced to the level described above, and the state of the dispersed wax in the dispersion can be kept stable.

The wax particle dispersion may further contain a polyalcohol (which may be the same as any of examples of the polyalcohol listed below as additives that may be added to the hair styling composition of the present invention in addition to the ingredients (A) to (D)) or a sugar alcohol (such as sorbitol). When a polyalcohol or a sugar alcohol is added to the wax particle dispersion, the content of any of these materials in the wax particle dispersion is preferably from 1 to 10% by mass.

The wax particle dispersion can be prepared, for example, by a process that includes mixing wax with the nonionic surfactant (and optionally a polyalcohol or a sugar alcohol) to form an oil phase, stirring the oil phase while keeping it at 70 to 95° C., gradually adding water to the oil phase, and mixing them.

In order to successfully ensure the effect of the use of the ingredient (C), the content of the wax, which is contained in the wax particle dispersion as the ingredient (C), in the hair styling composition is preferably 0.1% by mass or more, more preferably 0.5% by mass or more, and preferably 10% by mass or less, more preferably 5% by mass or less.

In the process of preparing the hair styling composition, therefore, the wax particle dispersion as the ingredient (C) is preferably used in such an amount that the content of the wax in the hair styling composition falls within the above ranges.

In the hair styling composition of the present invention, (D) water is used as a solvent. The content of water as the ingredient (D) in the hair styling composition (including the content of water in the ingredient (C)) is preferably from 20 to 95% by mass.

Besides the ingredients described above, if necessary, the hair styling composition of the present invention may further contain any of various ingredients commonly added to hair cosmetics such as hair styling compositions. Such additives include, for example, a polyalcohol, a preservative, a pH adjusting agent, a chelating agent, an antioxidant, and a perfume material (including an essential oil and flower water such as *Rosa centifolia* flower water).

Examples of the polyalcohol include ethylene glycol, diethylene glycol, polyethylene glycol (less than 300,000 in average molecular weight), propylene glycol, dipropylene glycol, polypropylene glycol, glycerin, diglycerin, 1,3-propanediol, 1,3-butylene glycol, sorbitol, pentylene glycol, hexanediol, and caprylyl glycol. The content of the polyalcohol in the hair styling composition is, for example, from 0.1 to 20% by mass.

Examples of the preservative include hinokitiol, sodium benzoate, methyl paraoxybenzoate, propyl paraoxybenzoate, butyl paraoxybenzoate, phenoxyethanol, methylchloroisothiazolinone-methylisothiazolinone solution, and 2-methyl-4-isothiazolin-3-one. The content of the preservative in the hair styling composition is, for example, from 0.001 to 2% by mass.

Examples of the pH adjusting agent include acids such as citric acid, phosphoric acid, malic acid, tartaric acid, and lactic acid; and alkaline agents (such as the alkaline agents listed above for the neutralization of the acidic polymers in the ingredient (A)).

The hair styling composition of the present invention preferably has a pH of 4 to 8. Therefore, the pH adjusting agent may be used in the amount required to adjust the pH of the hair styling composition to the above value.

Examples of the chelating agent include ethylenediaminetetraacetic acid or a salt thereof, diethylenetriaminepentaacetic acid or a salt thereof, hydroxyethylethylenediaminetriacetic acid or a salt thereof, and hydroxyethanediphosphonic acid or a salt thereof. The content of the chelating agent in the hair styling composition is preferably from 0.01 to 1% by mass.

Examples of the antioxidant include tocopherol and dibutylhydroxytoluene. The content of the antioxidant in the hair styling composition is preferably from 0.01 to 1% by mass.

Besides the above additives, the hair styling composition of the present invention may further contain a lower alcohol (such as ethanol or isopropanol), a nonionic surfactant (such as polyoxyethylene cetyl ether or polyoxyethylene polyoxypropylene cetyl ether), an oily ingredient (such as an ester, a vegetable oil, a fatty acid such as stearic acid, hydroxystearic acid, and myristic acid, a wax such as beeswax, a higher alcohol such as cetanol) that is solid at room temperature, a coloring material, an ultraviolet absorber, a plant extract, or other additives (the nonionic surfactant may be added independently of that contained in the wax particle dispersion).

The hair styling composition of the present invention may be in any form including, but is not limited to, a gel, a cream, or an emulsion. Also, a raw liquid comprising the hair styling composition of the present invention may be mixed with a propellant such as LPG. In this case, the obtained mixture may be charged into a container to provide a foam-type hair styling composition or may be charged into a container to provide a spray-type hair styling composition. In addition, when the hair styling composition of the present invention is an emulsion or the like, the hair styling composition may be charged into a container without being mixed with a propellant, so that a mist-type hair styling composition is provided.

The hair styling composition of the present invention can be used in such a way that an appropriate amount of the composition is taken up on a palm of a hand and applied to dry hair, and then used to style hair, or an appropriate amount of the composition is sprayed and applied onto dry hair, and then used to style hair.

EXAMPLES

Hereinafter, the present invention will be more specifically described based on examples. It will be understood that the examples described below are not intended to limit the present invention. In Tables 1 to 3 below, the content of each ingredient is in units of % so that the total amount of each hair styling composition is normalized to 100%. The unit % is always "% by mass". Also, in Tables 1 to 3 below, the unit % is omitted, and only the number is used to indicate the content of each ingredient. Further, in the examples, "%" is on a mass basis (% by mass) unless otherwise specified.

Examples 1 to 6 and Comparative Examples 1 to 6

The hair styling compositions of Examples 1 to 6 and Comparative Examples 1 to 6 were prepared using the ingredients shown in Tables 1 and 2, and then evaluated by the method described below.

Five expert evaluators each took up 1 g of the hair styling composition on the palm of the hand and applied it to the hair (dry hair) of a single subject. Subsequently, the five evaluators each evaluated the shine (wet-look shine) of the hair after hair styling and the ease of styling the hair (ease of handling the hair) after the application of the hair styling composition in comparison with the case that the hair styling composition of Comparative Example 1 was used, and each gave a score according to the evaluation criteria below.

(Evaluation Criteria of the Shine of Hair after Hair Styling and the Ease of Styling Hair)

2 points: Much better than when the hair styling composition of Comparative Example 1 is used.

1 point: Better than when the hair styling composition of Comparative Example 1 is used.

0 points: Substantially the same as when the hair styling composition of Comparative Example 1 is used.

−1 point: Worse than when the hair styling composition of Comparative Example 1 is used.

−2 points: Much worse than when the hair styling composition of Comparative Example 1 is used.

The scores given by all the evaluators were totaled for each hair styling composition. The resulting total for each hair styling composition was used as a measure of the shine of the hair after the hair styling and a measure of the ease of styling the hair, respectively.

Tables 1 and 2 show the evaluation results together with the appearance (form) of each hair styling composition. In Tables 1 and 2, the "Euphorbia Cerifera (Candelilla) wax particle dispersion" contains Euphorbia Cerifera (Candelilla) wax, POE (10) cetyl ether, and water. The Euphorbia Cerifera (Candelilla) wax particle dispersion contains 10% of Euphorbia Cerifera (Candelilla) wax and 10% of POE (10) cetyl ether, and water makes up the remaining 80%. Also, in the "Euphorbia Cerifera (Candelilla) wax particle dispersion", the volume average particle size of the Euphorbia Cerifera (Candelilla) wax is 100 nm or less as measured by a laser diffraction method using Microtrac MT3000 manufactured by NIKKISO CO., LTD. (the same applies to each Example and each Formulation Example described below). The Euphorbia Cerifera (Candelilla) wax particle dispersions were prepared by a process including mixing Euphorbia Cerifera (Candelilla) wax with POE (10) cetyl ether to form an oil phase, keeping the oil phase at about 80° C., gradually adding water to the oil phase under stirring, and then naturally cooling the mixture.

TABLE 1

| Ingredients | | Example | | | | | |
|---|---|---|---|---|---|---|---|
| | | 1 | 2 | 3 | 4 | 5 | 6 |
| (A) | Carboxyvinyl polymer | 1.0 | 1.0 | 1.0 | 0.5 | 1.0 | 1.0 |
| | 2-Amino-2-methyl-1-propanol | 0.7 | 0.7 | 0.7 | 0.35 | 0.7 | 0.7 |
| | POE (10) cetyl ether | — | — | — | — | — | — |
| (B) | Acrylic resin alkanolamine | 2 | 2 | 2 | 2 | 4 | 0.5 |
| (C) | Euphorbia Cerifera (Candelilla) wax particle dispersion | 15 | 30 | 5 | 15 | 15 | 15 |
| | Euphorbia Cerifera (Candelilla) wax | — | — | — | — | — | — |
| (D) | Water | Balance for a total of 100 | Balance for a total of 100 | Balance for a total of 100 | Balance for a total of 100 | Balance for a total of 100 | Balance for a total of 100 |
| | 1,3-Butylene glycol | 5 | 5 | 5 | 5 | 5 | 5 |
| | Ethylenediaminetetraacetic acid disodium dihydrate salt | 0.1 | 0.1 | 0.1 | 0.1 | 0.1 | 0.1 |
| | Ethanol | 1 | 1 | 1 | 1 | 1 | 1 |
| | Form | Translucent gel | Translucent gel | Translucent gel | Translucent gel | Translucent gel | Translucent gel |
| Evaluations | Shine of hair | 8 | 10 | 4 | 9 | 5 | 8 |
| | Ease of styling | 10 | 6 | 3 | 4 | 2 | 4 |

TABLE 2

| Ingredients | | Comparative Example | | | | | |
|---|---|---|---|---|---|---|---|
| | | 1 | 2 | 3 | 4 | 5 | 6 |
| (A) | Carboxy vinyl polymer | 1.0 | — | 1.0 | 0.1 | 1.0 | — |
| | 2-Amino-2-methyl-1-propanol | 0.7 | — | 0.7 | 0.07 | 0.7 | — |
| | POE (10) cetyl ether | — | 0.5 | — | 0.5 | 0.5 | — |
| (B) | Acrylic resin alkanolamine | 2 | 2 | 2 | 2 | 2 | 2 |
| (C) | Euphorbia Cerifera (Candelilla) wax particle dispersion | — | — | — | — | — | 30 |
| | Euphorbia Cerifera (Candelilla) wax | — | 1.5 | 1.5 | 1.5 | 1.5 | — |
| (D) | Water | Balance for a total of 100 | Balance for a total of 100 | Balance for a total of 100 | Balance for a total of 100 | Balance for a total of 100 | Balance for a total of 100 |
| | 1,3-Butylene glycol | 5 | 5 | 5 | 5 | 5 | 5 |
| | Ethylenediaminetetraacetic acid disodium dihydrate salt | 0.1 | 0.1 | 0.1 | 0.1 | 0.1 | 0.1 |
| | Ethanol | 1 | 1 | 1 | 1 | 1 | 1 |
| | Form | Gel | Cloudy emulsion | Not miscible | Cloudy emulsion and gel | Cloudy gel | Slightly cloudy liquid and gel |
| Evaluations | Shine of hair | (0) | 2 | — | 2 | −2 | −6 |
| | Ease of styling | (0) | −8 | — | −4 | 4 | −8 |

In Tables 1 and 2, the wording "balance for a total of 100" in the boxes for water means that water is added in such an amount that the sum of the amount of water and the total amount of all the ingredients other than water for the hair styling composition reaches 100% (the same applies to Table 3 below). Also, the term "acrylic resin alkanolamine" in Tables 1 and 2 refers to (alkyl acrylate/diacetone acrylamide) copolymer AMP (the same applies to Table 3 below).

As shown in Tables 1 and 2, the ease of styling the hair was better when each of the hair styling compositions of Examples 1 to 6 containing the ingredients (A) to (D) was used than when the reference product, namely, the hair styling composition of Comparative Example 1 (the hair styling composition free of the ingredient (C)) was used. The shine (wet-look shine) of the hair was also better after the hair styling with each of the hair styling compositions of Examples 1 to 6 than after that with the hair styling composition of Comparative Example 1. Therefore, the hair styling compositions of Examples 1 to 6 were superior in the function to add shine to the hair.

In contrast, the hair styling composition of Comparative Example 2, in which POE (10) cetyl ether was used instead of the ingredient (A) and Euphorbia Cerifera (Candelilla) wax was used without being formed into a dispersion, was inferior in the ease of styling the hair. Also, in the hair styling compositions of Comparative Examples 3 to 5, Euphorbia Cerifera (Candelilla) wax was used without being formed into a dispersion. Among them, particularly in the preparation of the hair styling composition of Comparative Example 3, it was not possible to uniformly disperse or mix the wax. Therefore, the above evaluations were not performed on the hair styling composition of Comparative Example 3. In the hair styling compositions of Comparative Examples 3 to 5, the hair styling compositions of Comparative Examples 4 and 5 were produced using POE (10) cetyl ether. Among them, the hair styling composition of Comparative Example 4 with a lower content of the ingredient (A) was inferior in the ease of styling the hair, and the hair styling composition of Comparative Example 5, in which the content of the ingredient (A) was the same as that in the hair styling composition of Example 1, was inferior in the shine of the hair after the hair styling. Further, the hair styling composition of Comparative Example 6, prepared without the ingredient (A), was inferior in both the shine of the hair after the hair styling and the ease of styling the hair.

Examples 7 and 8 and Comparative Examples 7 and 8

The hair styling compositions of Examples 7 and 8 and Comparative Examples 7 and 8 were prepared using the ingredients shown in Table 3 and then evaluated by the method described below.

Five expert evaluators each took up 1 g of the hair styling composition on the palm of the hand and applied it to the hair (dry hair) of a single subject. Subsequently, the five evaluators each evaluated the shine (wet-look shine) and lightness (low stickiness) of the hair after hair styling, and the ease of styling the hair (ease of handling the hair) after the application of the hair styling composition in comparison with the case that the hair styling composition of Comparative Example 7 was used, and each gave a score according to the evaluation criteria below.

(Evaluation Criteria of the Shine and Lightness of Hair after Hair Styling, and the Ease of Styling Hair)

2 points: Much better than when the hair styling composition of Comparative Example 7 is used.
1 point: Better than when the hair styling composition of Comparative Example 7 is used.
0 points: Substantially the same as when the hair styling composition of Comparative Example 7 is used.
−1 point: Worse than when the hair styling composition of Comparative Example 7 is used.
−2 points: Much worse than when the hair styling composition of Comparative Example 7 is used.

The scores given by all the evaluators were totaled for each hair styling composition. The resulting total for each hair styling composition was used as a measure of the shine of the hair after the hair styling, a measure of the lightness of the hair after the hair styling, and a measure of the ease of styling the hair, respectively.

Table 3 shows the evaluation results together with the appearance (form) of each hair styling composition.

the ingredients (A) to (D), was used than when the reference product, namely, the hair styling composition of Comparative Example 7 (free of the ingredient (C)) was used. The shine (wet-look shine) of the hair was also better after the hair styling with each of the hair styling compositions of Examples 7 and 8 than after that with the hair styling composition of Comparative Example 7. Namely, the hair styling compositions of Examples 7 and 8 were superior in the function to add shine to the hair.

The hair styling compositions of Examples 1 to 6 were prepared in the form of a gel, whereas the hair styling compositions of Examples 7 and 8 containing a liquid oil (liquid paraffin) were prepared in the form of a cream. The hair was light and less sticky (in other words, the hair was prevented from being appear oily or heavy) after the hair styling with each of the hair styling compositions of Examples 7 and 8 although they contained a liquid oil.

In contrast, the hair styling composition of Comparative Example 8, in which Euphorbia Cerifera (Candelilla) wax was used without being formed into a dispersion, was inferior in both the ease of styling the hair and the lightness of the hair after the hair styling.

Examples 9 and 10

Cream-Type Hair Styling Compositions

The hair styling compositions of Examples 9 and 10 were prepared using the ingredients shown below.

Example 9

| | |
|---|---|
| *Tamarindus indica* seed gum | 0.1% (ingredient (A)) |
| Carboxyvinyl polymer | 0.2% (ingredient (A)) |
| Potassium hydroxide | proper amount (ingredient (A)) |
| (Alkyl acrylate/diacetone acrylamide) copolymer AMP | 1.0% (ingredient (B)) |
| Liquid paraffin | 5.0% (ingredient (B)) |

TABLE 3

| | | Example | | Comparative Example | |
|---|---|---|---|---|---|
| Ingredients | | 7 | 8 | 7 | 8 |
| (A) Carboxyvinyl polymer | | 0.1 | 0.1 | 0.1 | 0.1 |
| Acrylic acid/alkyl methacrylate copolymer | | 0.3 | 0.3 | 0.3 | 0.3 |
| 2-Amino-2-methyl-1-propanol | | 0.2 | 0.2 | 0.2 | 0.2 |
| (B) Liquid paraffin | | 40 | 40 | 40 | 40 |
| Acrylic resin alkanolamine | | — | 1 | — | — |
| (C) *Euphorbia Cerifera* (*Candelilla*) wax particle dispersion | | 10 | 10 | — | — |
| *Euphorbia Cerifera* (*Candelilla*) wax | | — | — | — | 1 |
| (D) Water | | Balance for a total of 100 | Balance for a total of 100 | Balance for a total of 100 | Balance for a total of 100 |
| 1,3-Butylene glycol | | 5 | 5 | 5 | 5 |
| Ethylenediaminetetraacetic acid disodium dihydrate salt | | 0.1 | 0.1 | 0.1 | 0.1 |
| Ethanol | | — | 1 | — | — |
| Form | | Cream | Cream | Cream | Cream |
| Evaluations | Shine of hair | 7 | 7 | (0) | 2 |
| | Ease of styling | 6 | 8 | (0) | −5 |
| | Lightness | 0 | 0 | (0) | −6 |

In Table 3, the "acrylic acid/alkyl methacrylate copolymer" has 10 to 30 carbon atoms in the alkyl group of alkyl methacrylate.

The ease of styling the hair was better when each of the hair styling compositions of Examples 7 and 8, containing -continued

| | |
|---|---|
| *Euphorbia Cerifera* (*Candelilla*) wax particle dispersion | 5.0% (ingredient (C)) |

| | |
|---|---|
| Water | balance for a total of 100% (ingredient (D)) |
| Stearic acid | 3.0% |
| Hydroxystearic acid | 0.5% |
| POE (15) cetyl ether | 3.0% |
| POE (5.5) cetyl ether | 3.0% |
| Beeswax | 1.0% |
| 1,3-Butylene glycol | 5.0% |
| Preservative | proper amount |
| Ethanol | 1.0% |
| Perfume material | proper amount |

As regards water in Example 9, the wording "balance for a total of 100%" means that water is added in such an amount that the sum of the amount of water and the total amount of all the ingredients other than water for the hair styling composition reaches 100% (the same applies to each Example and Formulation Example described below).

Example 10

| | |
|---|---|
| *Tamarindus indica* seed gum | 0.1% (ingredient (A)) |
| Carboxyvinyl polymer | 0.2% (ingredient (A)) |
| Potassium hydroxide | proper amount (ingredient (A)) |
| (Alkyl acrylate/diacetone acrylamide) copolymer AMP | 1.0% (ingredient (B)) |
| Liquid paraffin | 5.0% (ingredient (B)) |
| Beeswax particle dispersion | 5.0% (ingredient (C)) |
| Water | balance for a total of 100% (ingredient (D)) |
| Stearic acid | 3.0% |
| Hydroxystearic acid | 0.5% |
| POE (15) cetyl ether | 3.0% |
| POE (5.5) cetyl ether | 3.0% |
| Beeswax | 1.0% |
| 1,3-Butylene glycol | 5.0% |
| Preservative | proper amount |
| Ethanol | 1.0% |
| Perfume material | proper amount |

The term "beeswax particle dispersion" used in the hair styling composition of Example 10 was prepared by the same method as that for the Euphorbia Cerifera (Candelilla) wax particle dispersion used in the hair styling composition of Example 1, except that beeswax was used instead of Euphorbia Cerifera (Candelilla) wax (the same applies to each example described below).

The hair styling compositions of Examples 9 and 10 were each applied to the hair of a subject in the same way as that for the hair styling composition of Example 1. As a result, the ease of styling the hair (ease of handling the hair) and the shine (wet-look shine) and lightness (low stickiness) after the hair styling were good both when the hair styling composition of Example 9 containing a Euphorbia Cerifera (Candelilla) wax particle dispersion was used and when the hair styling composition of Example 10 containing a beeswax particle dispersion was used.

Formulation Example 1

Foam-Type Hair Styling Composition

A raw liquid is prepared using the ingredients shown below. The raw liquid and a propellant (LPG) are mixed in a ratio of 90:10 (mass ratio) to form a hair styling composition of Formulation Example 1.

Raw Liquid for Hair Styling Composition of Formulation Example 1

| | |
|---|---|
| Hydroxyethyl cellulose | 0.1% (ingredient (A)) |
| Highly polymerized polyethylene glycol (2,000,000 in average molecular weight) | 0.05% (ingredient (A)) |
| *Butyrospermum parkii* (shea butter) oil | 0.5% (ingredient (B)) |
| Dimethicone | 0.5% (ingredient (B)) |
| Cetyl 2-ethylhexanoate | 1.0% (ingredient (B)) |
| Hydroxyethyl acrylate/methoxyethyl acrylate copolymer solution | 0.5% (ingredient (B)) |
| *Euphorbia Cerifera* (*Candelilla*) wax particle dispersion or beeswax particle dispersion | 8.0% (ingredient (C)) |
| Water | balance for a total of 100% (ingredient (D)) |
| POE (20) cetyl ether | 1.0% |
| Myristic acid | 3.0% |
| Cetanol | 0.5% |
| 1,3-Butylene glycol | 3.0% |
| 2-Amino-2-methyl-1-propanol | proper amount |
| Preservative | proper amount |
| Perfume material | proper amount |

In Formulation Example 1, the term "Euphorbia Cerifera (Candelilla) wax particle dispersion or beeswax particle dispersion" means that either one of these materials may be used (the same applies to Formulation Example 2 shown below). In both cases when the hair styling composition containing the Euphorbia Cerifera (Candelilla) wax particle dispersion is used and when the hair styling composition containing the beeswax particle dispersion is used, the ease of styling hair (ease of handling the hair) and the shine (wet-look shine) after hair styling are good as when the hair styling compositions of Examples 9 and 10 are used.

Formulation Example 2

Mist-Type Hair Styling Composition

A hair styling composition of Formulation Example 2 is prepared using the ingredients shown below.

Formulation Example 2

| | |
|---|---|
| Hydroxypropyl cellulose | 0.005% (ingredient (A)) |
| (Alkyl acrylate/diacetone acrylamide) copolymer AMP | 1.0% (ingredient (B)) |
| *Euphorbia Cerifera* (*Candelilla*) wax particle dispersion or beeswax particle dispersion | 8.0% (ingredient (C)) |
| Water | balance for a total of 100% (ingredient (D)) |
| Propylene glycol | 5.0% |
| *Rosa centifolia* flower water | 5% |
| Ethanol | 1.0% |
| Preservative | proper amount |
| Perfume material | proper amount |

In both cases when the hair styling composition of Formulation Example 2 containing the Euphorbia Cerifera (Candelilla) wax particle dispersion is used and when the hair styling composition of Formulation Example 2 containing the beeswax particle dispersion is used, the ease of styling hair (ease of handling the hair) and the shine (wet-look shine) after hair styling are good as when the hair styling compositions of Examples 9 and 10 are used.

What is claimed is:

1. A hair styling composition, comprising:
(A) a thickener;
(B) a hair fixative polymer, and optionally a liquid oil;
(C) a wax particle dispersion consisting of:
  wax consisting of dispersed wax particles having a volume average particle size of 500 nm or less,
  at least one nonionic surfactant selected from the group consisting of polyoxyethylene cetyl ether and polyoxyethylene polyoxypropylene cetyl ether, wherein the content of the nonionic surfactant(s) in the wax particle dispersion is 100-300 parts by mass based on 100 parts by mass of the wax,
  water, and
  one or more polyalcohols selected from the group consisting of ethylene glycol, diethylene glycol, propylene glycol, glycerin, diglycerin, 1,3-propanediol, 1,3-butylene glycol, sorbitol, pentylene glycol, hexanediol, and caprylyl glycol, wherein the content of the one or more polyalcohols is 1 to 10 parts by mass based on 100 parts by mass of the dispersion; and
(D) water.

2. The hair styling composition according to claim 1, wherein the nonionic surfactant has a hydrophile-lipophile balance (HLB) value of 11.0-16.0.

3. The hair styling composition according to claim 1, wherein the content of the nonionic surfactant in the wax particle dispersion (C) is 100-250 parts by mass based on 100 parts by mass of the wax.

4. The hair styling composition according to claim 1, wherein the content of the nonionic surfactant in the wax particle dispersion (C) is 100-120 parts by mass based on 100 parts by mass of the wax.

5. The hair styling composition according to claim 1, wherein the thickener (A) is a salt of an acidic polymer and 2-amino-2-methyl-1-propanol.

6. The hair styling composition according to claim 1, wherein the hair fixative polymer (B) is selected from the group consisting of an (alkyl acrylate/diacetone acrylamide) copolymer AMP and a hydroxyethyl acrylate/methoxyethyl acrylate copolymer.

7. The hair styling composition according to claim 1, wherein the nonionic surfactant consists of polyoxyethylene cetyl ether and polyoxyethylene polyoxypropylene cetyl ether.

8. The hair styling composition according to claim 1, wherein the thickener (A) is selected from the group consisting of a salt of a carboxyvinyl polymer, a salt of an acrylic acid/alkyl methacrylate copolymer, and a highly polymerized polyethylene glycol having an average molecular weight of 2,000,000 or more.

9. The hair styling composition according to claim 1, wherein the thickener (A) is a salt of a carboxyvinyl polymer.

10. The hair styling composition according to claim 1, wherein the component (B) comprises a hair fixative polymer and a liquid oil.

* * * * *